(12) United States Patent
Baugh

(10) Patent No.: US 10,695,580 B1
(45) Date of Patent: Jun. 30, 2020

(54) GANZFELD CONTACT LENSES

(76) Inventor: Thomas Kim Baugh, Denison, TX (US)

( * ) Notice: Subject to any disclaimer, the term of this patent is extended or adjusted under 35 U.S.C. 154(b) by 3044 days.

(21) Appl. No.: 12/653,367

(22) Filed: Dec. 11, 2009

(51) Int. Cl.
| | | |
|---|---|---|
| *A61N 5/06* | (2006.01) | |
| *A61M 21/00* | (2006.01) | |
| *A61B 5/16* | (2006.01) | |
| *A61F 9/008* | (2006.01) | |

(52) U.S. Cl.
CPC ............ *A61N 5/0618* (2013.01); *A61B 5/16* (2013.01); *A61M 21/00* (2013.01); *A61F 2009/00872* (2013.01); *A61M 2021/0044* (2013.01)

(58) Field of Classification Search
USPC ................ 600/27; 351/159.01–159.81, 160
See application file for complete search history.

(56) References Cited

U.S. PATENT DOCUMENTS

| | | | | |
|---|---|---|---|---|
| 3,476,499 A | * | 11/1969 | Wichterle | .......................... 8/507 |
| 4,388,918 A | * | 6/1983 | Filley | ............................... 600/27 |
| 4,570,626 A | * | 2/1986 | Norris et al. | ................... 128/858 |
| 4,777,937 A | * | 10/1988 | Rush et al. | ....................... 600/27 |
| 5,308,246 A | * | 5/1994 | Balocco | .......................... 434/236 |
| 6,123,081 A | * | 9/2000 | Durette | ........................... 128/858 |
| 6,281,192 B1 | * | 8/2001 | Leahy | .................. A61K 9/0048 |
| | | | | 514/20.8 |
| 2006/0268946 A1 | * | 11/2006 | Levatter | ............... A61B 18/203 |
| | | | | 372/6 |
| 2009/0093780 A1 | * | 4/2009 | Tuitupou | ............... A61F 9/0017 |
| | | | | 604/294 |
| 2010/0068141 A1 | * | 3/2010 | Kaushal | ............... A61K 31/121 |
| | | | | 514/1.1 |

OTHER PUBLICATIONS

Kooijman, A.C., The Homogeneity of the Retinal Illumination Restricted by Some ERG Lenses. Investigative ophthalmology & Visual Science (Mar. 1986).*

Siegel, IM. A Ganzfeld contact lens electrode. Am J Ophthalmol. Aug. 1975; 80(2):296-8.*

9mmSFX Theatrical Contact Lenses Website, "Blind Eye," accessed online Nov. 23, 2013, available online Mar. 24, 2008 at http://02a5349.netsolstores.com/blindeye.aspx.*

* cited by examiner

*Primary Examiner* — Kaylee R Wilson
(74) *Attorney, Agent, or Firm* — Robert E. Wise

(57) ABSTRACT

A method for inducing a Ganzfeld experience comprises placing full-field opaque or translucent contact lenses on all functioning eyes of a first person. After allowing a period of time to pass for the Ganzfeld effect to occur, a second person may monitor, question, or counsel the first person. The second person may engage the first person in massage or sensual activity, or may investigate psi phenomenon. The second person may physically control or torture the first person. The second person may perform a medical, ophthalmic, or dental procedure on the first person. The contact lenses may be used as a vehicle to apply a drug or other medicant to the first person's eyes.

14 Claims, No Drawings

GANZFELD CONTACT LENSES

BACKGROUND OF THE INVENTION

Described and named in the late 1920's by the psychologist Wolfgang Metzger, the word "Ganzfeld" is used to describe a featureless field of view and has been used to describe conditions that include the visual perception experienced in dense fog, unlit caves, and the cloudless sky. Devices currently in use to create a Ganzfeld include featureless hemispheres as in the Goldmann-Weeks Adaptometer for night vision evaluation, opaque goggles, and bisected ping-pong or tennis balls. Fully opaque contact lenses exist for occlusive treatment of monocular eye conditions such as monocular treatment of amblyopia, extreme photosensitivity in pathology of an eye, and for the treatment of intractable diplopia. Binocular occlusive lenses have been used for theatrical effect.

A "Ganzfeld effect" is a phenomenon of visual perception caused by staring at an undifferentiated and uniform field of color, including black. The effect is a loss of vision, apparent blindness, as the brain cuts off the unchanging signal from the eyes. The Ganzfeld effect may give rise to hallucinations or other psychological effects.

Several patents exist which describe "opaque" contact lenses. The disclosures of these patents are, however, limited to lenses with opaque portions that allow for vision around or through the lenses. Opaque contact lens patents describe cosmetic lenses made to alter the perceived color of the iris of the eye and feature a central transparent aperture to allow vision through the lenses. Monocular fully opaque lenses have been described for treatment of amblyopia and the monocular sensation of intractable photic sensitivity and pain. Some opaque lens patents describe opaque portions of a lens for rehabilitation of visual field loss, or to provide new or multiple apertures for low vision treatment.

Prior art devices used to create a Ganzfeld, such as goggles and hemispheres, offer an incomplete effect due to physical aspects of the goggles or hemispheres used.

BRIEF SUMMARY OF THE INVENTION

This invention is the binocular use of full-field opaque and full-field translucent contact lenses for the creation of a colored, black, or white Ganzfeld in a user. The full-field opaque contact lenses or the full-field translucent contact lenses are placed on the cornea of the user's eyes. A contact lens of this invention would produce a Ganzfeld that would not vary with eye movement or position.

This invention will improve the creation and quality of the Ganzfeld experience, and will increase the applications, uses, and popularity of the Ganzfeld experience by the employment of novel opaque and translucent contact lenses for this purpose. The result of this improvement is a non-drug reversible sensory modification in the wearer.

The present invention utilizes two full-field opaque contact lenses for bi-ocular use in creation of a complete Ganzfeld in the normal two-eyed wearer. Where the user has only one functioning eye, only one opaque or translucent contact lens would be required.

The lens design is suitable for any contact lens material, in rigid or soft lenses, preferably in a one-day-use disposable soft contact lens. Optical lens power is not a feature and the lens may be considered non-refractive. The color of the lens used may be of any color of the visible spectrum including white and black. In order to create the most effective Ganzfeld, light may diffuse through the lenses, but not enough light for the user to perceive external detail.

Lens colors may be chosen to produce certain desired effects. Blue lenses and white lenses provide greater discernment of entoptic phenomena, due to light scatter and contrast, enhancing the self-perception of "floaters", vitreous anomalies, cataracts, and retinal vasculature. Black lenses would provide visual sensory deprivation, the visual experience of neural retinal phenomena and the perceptual experience of complete absence of light. Each color would have an application that could vary with the wavelength through the contact lens. Intensity of the transmission of light through the lens may be varied by (1) varying the color density of the contact lens, (2) by treating the surface of the contact lens, and (3) by use of various light sources directed upon the contact lenses of the wearer.

A different color worn and experienced in each eye could aid in detection of the source of various ocular and neuro-ocular phenomena. U.S. Pat. No. 4,388,918 to Filley describes creation of "mental harmonization" by use of complementary color fields projected to each eye. This mental harmonization could be created by having the user wear a different colored translucent contact lens in each eye.

DETAILED DESCRIPTION OF THE PREFERRED EMBODIMENT

The full-field opaque lens extends to cover the cornea of the eye and not allow peripheral or central light to enter the eye. Design of the contact lens should allow for no focused peripheral vision around the diameter of the opaque aspect of the lens. This calls for a large diameter contact lens with the opaque lens area to or beyond the extent of the limbus of the cornea in all 360 degrees of field. The lens could be fully tinted edge-to-edge or offset within the total diameter of the lens. Generally, this calls for a lens occlusion of 12 through 18 millimeters in diameter. A less-than-optimal Ganzfeld is created by a lens that allows peripheral or central vision in any way around or through the lens.

In circular contact lens designs, this invention would usually require 12 to 18 millimeters overall diameter contact lenses. Non-circular lenses would also exhibit similar color distribution relative to the overall lens dimensions in order to produce the full-field occlusion. Full scleral coverage contact lenses could be employed to accomplish this invention. Full sclera coverage contact lenses have been described in dimensions of approximately 29.00 mm×26.50 mm.

The Ganzfeld contact lenses can be made of at least one of any soft, hard, membrane, gas-permeable contact lens material, and a dissolvable eye shield material. For translucent lenses, the lens may be colored or fluorescent colored.

The uses of Ganzfeld contact lenses are many and would include all current Ganzfeld uses employing techniques other than contact lenses. These include, but are not limited to, sensory deprivation, an aid to hypnosis, guided mental imagery, concentration, habit cessation, counseling, hallucinations, blindness simulation, mood alteration, meditation, heightened sensorium of the other senses, enjoyment of music, sound and the spoken word. Another Ganzfeld use to which this invention could be applied is psi research, where any statistical deviation from pure chance might tend to prove an effect.

Because the wearer may be able to have greater freedom of movement, new Ganzfeld contact lens uses could include, but are not limited to, orientation and mobility training for experience of vision loss, altitudinal head tilt position effect upon the evaluation of entoptic phenomena including vitreous detachment and retinal features, and a heightened appreciation of the non-visual senses and sensual experiences.

The wearing of Ganzfeld contact lenses could eliminate the need for a bowl device in dark adaptometry testing, simplifying the test procedure. Non-bowl dark adaptometry testing could be performed at a lower cost without the specialized and costly test device.

Ganzfeld contact lenses could function as a protective light shield and barrier for medical, dental, and surgical procedures performed near the eye or adnexa while barring the view of the proceedings from the patient. Ganzfeld contact lenses may be used upon animal eyes, for instance to allow less stress in performance of veterinary procedures.

In regard to sensory deprivation, the duration of the experience would greatly influence the response. Brief experience in a non-threatening environment could be enjoyable and refreshing. But extended experience of sensory deprivation by use of Ganzfeld lenses could lead to distress and may be considered a form of torture or abuse. An investigatory tactic may employ Ganzfeld lenses to create the ruse of blindness in a detainee. The surreptitious placement of opaque contact lenses on a detainee's eyes under corneal anesthesia could cause a useful interrogation effect.

A remarkable and brief effect is experienced when the Ganzfeld lenses are removed. The restoration of vision is quite vivid and the colors exhibit an increased saturation and vibrancy. The regained sense of vision can be quite pleasing.

A method for producing a Ganzfeld effect or a Ganzfeld experience in a person is to place a full-field opaque contact lens on each functioning eye of the person. If the person has two functioning eyes, then full-field opaque contact lenses would be placed in each eye. If the person has only one functioning eye, then only one lens will be required for the functioning eye.

Another method for producing a Ganzfeld effect or a Ganzfeld experience in a person is to place a full-field translucent contact lens on each functioning eye of the person. If the person has two functioning eyes, then full-field translucent contact lenses would be placed in each eye. If the person has only one functioning eye, then only one lens will be required for the functioning eye. The translucent lens or lenses should be incapable of clarity, but should transmit and sufficiently diffuse light, so that objects in the visual field cannot be clearly seen.

Another method may include the step of placing on, or infusing into, the lenses a drug or other medicament prior to the step of placing the lenses in the person's eyes.

The Ganzfeld effect may produce in a wearer a Ganzfeld sensory modification including, but not limited to, heightened non-visual sensory awareness; self-observation of entoptic phenomena; a dream-like or hallucinogenic state; a heightened appreciation of at least one of music, meditation, massage, or sexual activity; a heightened ability to concentrate or pray; sensory deprivation; an altered state of consciousness; extra-sensory perception; and psi phenomenon.

Once the opaque or translucent lenses have been placed in all functioning eyes of the person, it is usually necessary to allow some time to pass for the Ganzfeld effect to occur. The amount of time necessary will depend on the particular person and the particular experience that is desired. Persons of ordinary skill in this art, with only routine experimentation, can determine the amounts of time necessary for any desired purpose.

Once the Ganzfeld effect begins in the person wearing the opaque or translucent lenses, hereafter called the patient, a second person can perform any or all of the following tasks: monitoring the patient; questioning the patient; counseling the patient; psychoanalyzing the patient; hypnotizing the patient; performing a medical, ophthalmic, or dental procedure on the patient; torturing or physically controlling the patient; investigating psi effects by telepathically communicating with the patient; or providing visual therapy to the patient. The wearer may also obtain heightened pleasure from receiving massage, engaging in sexual relations, or engaging in interpersonal or sensual relations. The wearer may also experience a useful alteration of sensorum.

The methods herein may include, after placement of the lenses in the person's eyes, exposing any part of the person's body to ultraviolet radiation for a time. The lenses would serve to protect the person's eyes from exposure to ultraviolet radiation.

The methods herein may further include the step of subsequently removing the opaque or translucent contact lenses from the eyes of the person.

All methods recited in this application can be performed on any animal, including human beings.

While the preferred embodiment teaches particular methods for practicing this invention, it is not meant to limit the invention. The scope of this invention is limited only by the following claims.

I claim:

1. A method of using Ganzfeld contact lenses comprising the steps of placing a first Ganzfeld contact lens on the cornea of one of the wearer's eyes and then placing a second Ganzfeld contact lens on the other of the wearer's eyes, wherein at least one of the Ganzfeld contact lenses placed on the cornea of an eye contains a drug that acts upon the eye during the time that the Ganzfeld contact lens is on the cornea of that eye.

2. The method of claim 1 wherein both Ganzfeld contact lenses are translucent.

3. The method of claim 1 wherein at least one of the two Ganzfeld contact lenses is both translucent and incapable of clarity, thereby creating a diffuse image of the ambient light.

4. The method of claim 1 wherein one of the two Ganzfeld contact lenses is opaque and the other is translucent, wherein the translucent Ganzfeld contact lens transmits and diffuses light so that objects in the visual field cannot be clearly seen.

5. The method of claim 1 further comprising the step of: subsequent to the placement of the Ganzfeld contact lenses on the wearer's eyes, the wearer is physically restrained.

6. The method of claim 1 further comprising the step of: subsequent to the placement of the Ganzfeld contact lenses on the wearer's eyes, the wearer is questioned by another person to elicit information from the wearer.

7. The method of claim 1 further comprising the step of: subsequent to the placement of the Ganzfeld contact lenses on the wearer's eyes, the wearer is tortured by another person to make the wearer more controllable or amenable to answering questions.

8. The method of claim 1 wherein both Ganzfeld contact lenses are translucent, and wherein at least one lens is one of colored and fluorescent colored.

9. The method of claim 1 further comprising the step of: subsequent to the placement of the Ganzfeld contact lenses on the wearer's eyes, hypnotizing the wearer.

10. The method of claim 1 further comprising the step of: subsequent to the placement of the Ganzfeld contact lenses on the wearer's eyes, having at least one other person counsel the wearer.

11. The method of claim 1 further comprising the steps of:
subsequent to the placement of the Ganzfeld contact lenses on the wearer's eyes, hypnotizing the wearer, and engaging the wearer in psychotherapeutic counseling.

12. A means for inducing in a human a Ganzfeld sensory modification, said means comprising plural Ganzfeld contact lenses for placement on the two eyes of the human, said Ganzfeld contact lenses being opaque, wherein the Ganzfeld contact lenses are made of at least one of any soft, hard, membrane, gas-permeable contact lens material, and a dissolvable eye shield material.

13. A method of using Ganzfeld contact lenses comprising the steps of placing a first Ganzfeld contact lens on the cornea of one of a wearer's eyes and then placing a second Ganzfeld contact lens on the other of the wearer's eyes, and subsequent to the placement of the Ganzfeld contact lenses on the wearer's eyes, exposing at least part of the wearer's body to ultraviolet radiation, thereby protecting the wearer's cornea from the ultraviolet radiation.

14. A means for inducing in a human a Ganzfeld sensory modification, said means comprising plural Ganzfeld contact lenses for placement on the two eyes of the human, said Ganzfeld contact lenses being opaque, wherein the two lenses are colored.

\* \* \* \* \*